United States Patent
Liu et al.

(10) Patent No.: US 12,374,460 B2
(45) Date of Patent: Jul. 29, 2025

(54) UNCERTAINTY ESTIMATION IN MEDICAL IMAGING

(71) Applicant: Siemens Healthineers AG, Forchheim (DE)

(72) Inventors: Jingya Liu, Harrison, NJ (US); Bin Lou, Princeton, NJ (US); Ali Kamen, Skillman, NJ (US)

(73) Assignee: Siemens Healthineers AG, Forchheim (DE)

( * ) Notice: Subject to any disclaimer, the term of this patent is extended or adjusted under 35 U.S.C. 154(b) by 577 days.

(21) Appl. No.: 17/662,897

(22) Filed: May 11, 2022

(65) Prior Publication Data

US 2023/0368913 A1    Nov. 16, 2023

(51) Int. Cl.
*G16H 50/20*    (2018.01)
*G16H 30/20*    (2018.01)

(52) U.S. Cl.
CPC ............. *G16H 50/20* (2018.01); *G16H 30/20* (2018.01)

(58) Field of Classification Search
CPC ...................................................... G06V 10/82
See application file for complete search history.

(56) References Cited

U.S. PATENT DOCUMENTS

| | | | | |
|---|---|---|---|---|
| 11,941,739 | B1 * | 3/2024 | Radzihovsky | ........ G06T 17/205 |
| 2021/0110534 | A1 * | 4/2021 | Yu | ......................... G06V 10/764 |
| 2021/0287780 | A1 * | 9/2021 | Korani | .................... G06N 3/045 |
| 2021/0407637 | A1 * | 12/2021 | Park | ........................ G16H 30/20 |
| 2022/0284585 | A1 * | 9/2022 | Holtzman Gazit | ........ G06T 7/11 |

FOREIGN PATENT DOCUMENTS

| | | | | |
|---|---|---|---|---|
| EP | 3712849 A1 | * | 9/2020 | ............ G06T 7/0012 |
| WO | WO-2022125090 A1 | * | 6/2022 | .............. G06T 7/269 |

OTHER PUBLICATIONS

Kohl, S.A., Romera-Paredes, B., Meyer, C., De Fauw, J., Ledsam, J.R., Maier-Hein, K.H., Eslami, S.M., Rezende, D.J. and Ronneberger, O., 2018. A probabilistic u-net for segmentation of ambiguous images. arXiv preprint arXiv:1806.05034.

Yan, W., Huang, L., Xia, L., Gu, S., Yan, F., Wang, Y. and Tao, Q., 2020. MRI manufacturer shift and adaptation: increasing the generalizability of deep learning segmentation for MR images acquired with different scanners. Radiology: Artificial Intelligence, 2(4), p. e190195.

(Continued)

*Primary Examiner* — Di Xiao

(57) ABSTRACT

For uncertainty estimation for a machine-learned model prediction in medical imaging, a distribution in latent space is sampled to determine uncertainty in machine-learned model prediction. For example, a segmentation is output by a machine-learned model in response to input of multi-parametric data. A latent space generated by the machine-learned model is used to estimate the uncertainty of the segmentation, such as a segmentation of a prostate lesion. The model of Kohl, et al., may be used as the variational auto encoder generates a latent space representing the distribution of the training data, which latent space may be used to determine uncertainty.

14 Claims, 4 Drawing Sheets
(2 of 4 Drawing Sheet(s) Filed in Color)

(56) References Cited

OTHER PUBLICATIONS

Gal, Y. and Ghahramani, Z., Jun. 2016. Dropout as a bayesian approximation: Representing model uncertainty in deep learning. In international conference on machine learning (pp. 1050-1059). PMLR. [5] Golan, I. and El-Yaniv, R., 2018. Deep anomaly detection using geometric transformations. arXiv preprint arXiv:1805.10917.

Gong, D., Liu, L., Le, V., Saha, B., Mansour, M.R., Venkatesh, S. and Hengel, A.V.D., 2019. Memorizing normality to detect anomaly: Memory-augmented deep autoencoder for unsupervised anomaly detection. In Proceedings of the IEEE/CVF International Conference on Computer Vision (pp. 1705-1714).

Liu, J.Z., Lin, Z., Padhy, S., Tran, D., Bedrax-Weiss, T. and Lakshminarayanan, B., 2020. Simple and principled uncertainty estimation with deterministic deep learning via distance awareness. arXiv preprint arXiv:2006.10108. [9] Kendall, A., Badrinarayanan, V. and Cipolla, R., 2015. Bayesian segnet: Model uncertainty in deep convolutional encoder-decoder architectures for scene understanding. arXiv preprint arXiv:1511.02680.

Yu, X., Lou, B., Shi, B., Winkel, D., Arrahmane, N., Diallo, M., Meng, T., von Busch, H., Grimm, R., Kiefer, B. and Comaniciu, D., Apr. 2020. False positive reduction using multiscale contextual features for prostate cancer detection In multi-parametric MRI scans. In 2020 IEEE 17th International Symposium on Biomedical Imaging (ISBI) (pp. 1355-1359). IEEE.

Wang, X., Peng, Y., Lu, L., Lu, Z., Bagheri, M. and Summers, R.M., 2017. Chestx-ray8: Hospital-scale chest x-ray database and benchmarks on weakly-supervised classification and localization of common thorax diseases. In Proceedings of the IEEE conference on computer vision and pattern recognition (pp. 2097-2106).

Quardini, K., Yang, H., Unnikrishnan, B., Romain, M., Garcin, C., Zenati, H., Campbell, J.P., Chiang, M.F., Kalpathy-Cramer, J., Chandrasekhar, V. and Krishnaswamy, P., 2019. Towards practical unsupervised anomaly detection on retinal images. In Domain Adaptation and Representation Transfer and Medical Image Learning with Less Labels and Imperfect Data (pp. 225-234). Springer, Cham.

Winkel, D.J., Wetterauer, C., Matthias, M.O., Lou, B., Shi, B., Kamen, A., Comaniciu, D., Seifert, H.H., Rentsch, C.A. and Boll, D.T., 2020. Autonomous detection and classification of PI-RADS lesions in an MRI screening population Incorporating multicenter-labeled deep learning and biparametric imaging: proof of concept. Diagnostics, 10(11), p. 951.

Winkel, D.J., Tong, A., Lou, B., Kamen, A., Comaniciu, D., Disselhorst, J.A., Rodriguez-Ruiz, A., Huisman, H., Szolar, D., Shabunin, I. and Choi, M.H., 2021. A novel deep learning based computer-aided diagnosis system improves the accuracy and efficiency of radiologists in reading biparametric magnetic resonance images of the prostate: results of a multireader, multicase study. Investigative Radiology, 56(10), pp. 605-613.

Golan, I. and El-Yaniv, R., 2018. Deep anomaly detection using geometric transformations. arXiv preprint arXiv:1805.10917.

Fort, S., Ren, J. and Lakshminarayanan, B., 2021. Exploring the Limits of Out-of-Distribution Detection. arXiv preprint arXiv:2106.03004.

Kendall, A., Badrinarayanan, V. and Cipolla, R., 2015. Bayesian segnet: Model uncertainty in deep convolutional encoder-decoder architectures for scene understanding. arXiv preprint arXiv:1511.02680.

\* cited by examiner

UNCERTAINTY ESTIMATION IN MEDICAL IMAGING

BACKGROUND

The present embodiments relate to machine-learned-based prediction in medical imaging. It is cumbersome and time-consuming for the radiologist to detect and label lesions manually. Artificial intelligence (AI)-driven automated detection frameworks may detect lesions, such as prostate cancer based on multi-parametric magnetic resonance imaging (MRI) (mp-MRI).

As deep learning-based methods are data-dependent, the AI lesion detector may predict overconfident results on the cases with different data distributions from the training data. As the MRIs are considered a standard image modality for PCa diagnosis, the scans can be acquired by various MRI scanners from different vendors, such as Siemens, GE, or Philips, with different machine settings and machine noise and can be processed by different protocols. Additionally, the different b-value settings may lead to intensity various of Apparent Diffusion Coefficient (ADC) images and Diffusion-Weighted Images (DWI). These artifacts of collected MRIs may cause systematical differences of the AI model trained with cases from specific settings. The lack of ability to distinguish the testing cases with different data distribution from training cases may lead to inaccurate prediction for the lesion location and the predicted lesion boundary in actual clinical diagnosis.

Out-of-distribution (OOD) detection algorithms learn data distributions of the training data directly. The out-of-distribution classes that do not belong to the existing training classes may be distinguished, such as distinguishing the scene understanding dataset for street view houses (SVHN) from CIFAR-100, which consists of objects (such as fish, flowers) and acquiring the semantical distribution of the input data by a discriminative network. Some other approaches aim at detecting the abnormal region on image or video, such as lesion detection on X-ray and disease screening on retinal images. However, these methods address the data with apparent abnormal regions or learnable data distribution. There are many cases where the data has inherent ambiguities, such as medical imaging applications. The lesions in medical images may have blurry lesion boundaries or insufficient information for scoring the level of suspicion that may cause various diagnoses. Independent pixel-wise prediction may be learned, and the uncertainty predicted by an ensemble of models via Monte Carlo dropout. However, this group of work learns the data independently and cannot guarantee that the variance is sufficiently learned.

Kohl, et al., in "A Probabilistic U-Net for Segmentation of Ambiguous Images," provide multiple segmentation hypotheses for ambiguous images via a Variational Auto-Encoder (VAE) conditional on the image. Instead of directly predicting pixel-wise probability via multiple models, the probabilistic U-Net learns the co-variance between pixels and is flexible enough to predict the joint probability of all pixels in the segmentation. This effectively learns the training data distributions, samples diverse possible lesion regions, and works well for predicting images that might lead to different expertise evaluations.

SUMMARY

Systems, methods, and instructions on computer readable media are provided for uncertainty estimation for a machine-learned model prediction in medical imaging. A distribution in latent space is sampled to determine uncertainty in machine-learned model prediction. For example, a segmentation is output by a machine-learned model in response to input of multi-parametric data. A latent space generated by the machine-learned model is used to estimate the uncertainty of the segmentation, such as a segmentation of a prostate lesion. The model of Kohl, et al., may be used as the variational auto encoder generates a latent space representing the distribution of the training data, which latent space may be used to determine uncertainty.

In a first aspect, a method is provided for lesion segmentation for a medical imager. The medical imager acquires multi-parametric data representing a patient. A machine-learned network generates a segmentation of a lesion represented in the multi-parametric data. The segmentation is generated in response to input of the multi-parametric data to the machine-learned network. An uncertainty of the segmentation is determined using the machine-learned network. The segmentation and the uncertainty of the segmentation are displayed.

In one embodiment, the medical imager is a magnetic resonance (MR) imager. The multi-parametric data is, for example, T2-weighted data, apparent diffusion coefficient data, and diffusion-weighted data. The multi-parametric data represents any of various regions of the patient, such as a prostate region. In a further approach, the segmentation of the lesion is a segmentation of a prostate lesion, which is generated in response to input of the T2-weighted data, apparent diffusion coefficient data, diffusion-weighted data, and a prostate mask.

In another embodiment, the machine-learned network is a U-Net with convolutional layers and an encoder. The multi-parametric data is input to both the U-Net and the encoder. A sample from a latent space at an output of the encoder is fed to one of the convolutional layers of the U-Net. The U-Net generates the segmentation based in part on the input of the multi-parametric data and in part on the sample from the latent space. As a further refinement, the U-Net is a residual U-Net (multi-scale), and the encoder is a conditional variational auto encoder. The sample from the latent space is concatenated with a last activation map of the residual U-Net. As another refinement, the segmentation and additional segmentations are generated. The additional segmentations are generated with different samples from the latent space. For example, the segmentation and additional segmentations are generated with samples being randomly sampled from the latent space. As a further example, a variance of the segmentation and additional segmentations is calculated as a heat map representing the uncertainty. In another refinement, a mean in the latent space is determined. The segmentation is generated based in part on the mean in the latent space, and the uncertainty is determined as a variation in the latent space. A heat map is output by the U-Net based in part on the variation.

In yet another embodiment, the machine-learned network generates the segmentation and additional segmentations. The uncertainty is determined as a variance of the segmentation and additional segmentations.

As another embodiment, the segmentation is displayed as a mean of multiple predictions by the machine-learned network, and the uncertainty is displayed as a heatmap by spatial location of the segmentation.

In a second aspect, a medical system is provided for uncertainty estimation. An imager is configured to capture scan data representing a patient. An image processor is configured to apply the scan data to a machine-learned network. The machine-learned network is configured to output a classification, detection, and/or segmentation in response to the application. The image processor is further configured to determine an uncertainty of the classification, detection, and/or segmentation with random samples from a latent space. A display is configured to display the classification, detection, and/or segmentation and to display the uncertainty.

In one embodiment, the imager is a magnetic resonance (MR) imager, and the scan data is multi-parametric MR data. The machine-learned network is configured to output the segmentation as a segmentation of a lesion, and the uncertainty is a heat map with greater uncertainty for some locations than others represented in the heat map.

As another embodiment, the machine-learned network is a U-Net and an encoder separate from the U-Net. The encoder is configured to generate the latent space. For example, the U-Net is configured to output a plurality of the classification, detection, and/or segmentation in response to the application of the scan data representing the patient using the random samples. The uncertainty is a variance of the plurality of the classification, detection, and/or segmentation. As a further refinement, the display of the classification, detection, and/or segmentation is display of a mean of the plurality. As another example, the uncertainty is the output based on a variance of the random samples.

In a third aspect, a method is provided for uncertainty determination in machine-learned prediction for a medical scanner. A machine-learned model generates multiple first predications for a patient based on input of scan data from the medical scanner to the machine-learned model. An uncertainty of the multiple first predictions is determined from random sampling of a latent space. A second prediction based on the multiple first predictions (e.g., a mean of the first predictions) and the uncertainty are displayed.

In one embodiment, the multiple first predictions are generated from the random sampling of the latent space. A variance of the multiple first predictions is determined as the uncertainty.

In another embodiment, a variance in the latent space is determined, and the uncertainty is generated based on the variance in the latent space.

Any one or more of the aspects described above may be used alone or in combination. Any aspects of one of method, system, or computer readable media may be used in the others of method, system, or computer readable media. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS

To assist in diagnosis, uncertainty in a prediction (e.g., segmentation, classification, or detection) is estimated. The training data distribution is learned, and the learned distribution is used to predict the uncertainty in prediction for a given patient. For example, uncertainty of an existing lesion detector for prostate lesion segmentation using multiparametric MR scan is estimated.

Inspired by Kohl, et al., and the ability of the predictor to predict multiple hypotheses, the machine-learned model may be used to estimate uncertainties. For example, the probabilistic U-Net of Kohl, et al., learns the co-variance pixel-level uncertainties on PCa lesion segmentation under testing cases with different distributions from the training case.

The uncertainty of the unknown dataset is explored. A given patient image may have multiple segmentation hypotheses for lesion detection due to the ambiguity of different data distributions. The proposed framework can detect abnormal areas and suspicious areas predicted as lesions. The uncertainty identifies the abnormal or suspicious areas. For example, U-Net or other machine-learned model tumor prediction and uncertainty prediction joint training provides an end-to-end training network that can directly and instantly obtain uncertainty through a set of sampled images. The latent space with large variance reflects the high degree of uncertainty in the prediction area.

The framework can be generalized to different tasks, such as classification, detection, and/or segmentation. The random sampling from the learned latent space provides a distribution of underlying factors that may impact the uncertainty of the prediction (e.g., lesion segmentation). The uncertainty is then an additional function of a computer-aided diagnosis (CAD) system (e.g., prostate MR) to provide radiologists highly suspicious regions where lesion borders are difficult to determine. This would also be useful for clinicians to identify the optimal location for biopsy.

Figure 1:
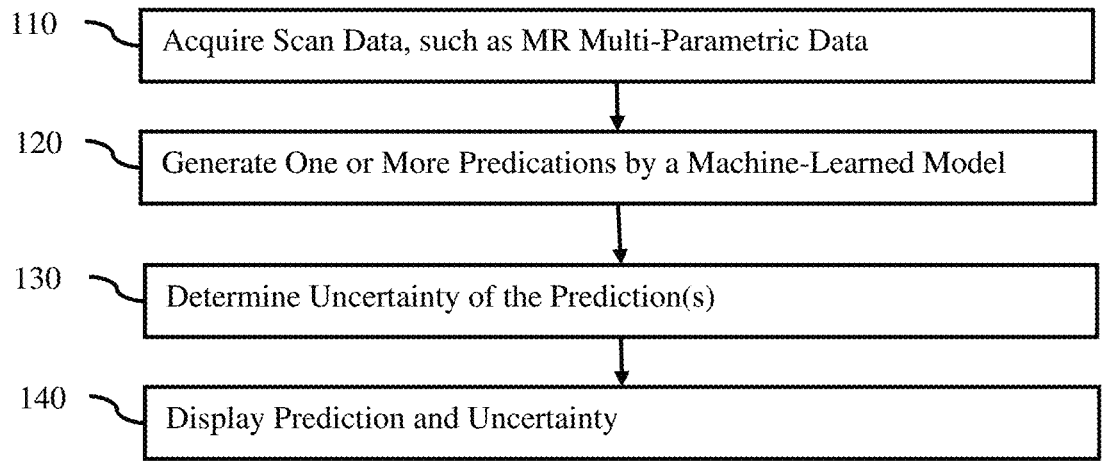
FIG. 1 is a flow chart diagram of one embodiment of a method for uncertainty determination for machine-learned predictions.

FIG. 1 is a flow chart diagram of one embodiment of a method for uncertainty determination in machine-learned prediction for a medical scanner. For example, the method is for lesion segmentation (e.g., PCa or prostate lesion). The AI or machine-learned model for prediction is used to determine uncertainty. Rather than a Monte-Carlo drop-out approach by varying the input data, the learned distribution is used to estimate uncertainty.

The method is performed by a medical imager, such as a magnetic resonance or computed tomography system. An image processor may acquire scan data, generate a prediction using a machine-learned model, determine uncertainty in the prediction (e.g., spatial variation in uncertainty), and/or generate an image for display on a display screen of the prediction and uncertainty. Other devices may be used, such as using a medical imager or memory to acquire the scan data. In other embodiments, a computer, server, or workstation with access to a memory or medical imager, performs the method.

The acts are performed in the order shown (numerical or top-to-bottom) or other orders. For example, act 130 is performed prior to or simultaneously with act 120. Additional, different, or fewer acts may be provided. For example, act 140 is not performed, such as where the uncertainty and prediction are stored in a patent electronic medical record. As another example, act 120 is not performed. Instead, the uncertainty is determined from variance in the latent space.

In act 110, a medical imager acquires scan data. The image processor acquires scan data by transfer from memory or over a computer network. In other embodiments, the scan data is acquired by scanning a patient. The medical imager may include an image processor that acquires the data.

In one embodiment, the scan data is imaging or image data representing the patient. The scan data may be at any stage of processing, such as acquired from an antenna or detector or after image processing (e.g., after filtering, detecting, reconstruction, and/or scan conversion). For example, the scan data is a reconstructed representation of an area or volume of the patient. As another example, the scan data is formatted as an image for display on a display screen.

Any type of medical imaging may be used. In one embodiment, the scan data is magnetic resonance (MR) data acquired by an MR imager or system. In the examples used herein, MR data for imaging a prostate is used. In other examples, MR of other regions of the patient, computed tomography (CT), ultrasound, optical, positron emission tomography, single photon emission computed tomography, x-ray, or other types of scanning and resulting scan data may be used.

In an example MR embodiment for detection of lesions or cancer in the prostate, the medical imager acquires multi-parametric data representing a patient. For example, T2-weighted data, apparent diffusion coefficient (ADC) data, and diffusion-weighted imaging (DWI) data are acquired. Additional, different, or fewer MR parameters may be acquired. In other embodiments, multi-parametric data for CT, ultrasound, or other type of imaging is used. In yet other embodiments, the multi-parametric data is data from different modalities (e.g., ultrasound and MR).

In act 120, an image processor generates one or more predictions. The prediction is a classification, segmentation, and/or detection. For example, the prediction is a segmentation as a boundary and/or pixel or voxel labels for locations belonging to an object, such as a prostate lesion.

The prediction is made by a machine-learned model. Any machine-learned model may be used, such as a neural network (e.g., fully connected or convolutional neural network). Other models may include support vector machine (SVM) or Bayesian models. The machine-learned model is of any of various architectures, such as U-Net, image-to-image, and/or encoder-decoder networks.

The machine-learned model generates one or more predictions for a patient based on input of the scan data with or without input of other data (e.g., clinical data for the patient). The scan data is input to an input layer of the machine-learned model, which generates the prediction in response to input.

The machine-learned model was previously trained, such as having learned values for learnable parameters of a defined architecture based on optimization minimizing a loss over a large number (e.g., hundreds, thousands, or more) samples of training data (i.e., example input scan data and corresponding output ground truth). The optimization of the values of the learnable parameters minimizing the loss between the outputs of the model and the ground truths given the input examples identifies or sets the values of the learnable parameters to be used in the trained model.

For training the machine-learned model, the machine learning model arrangement is defined. The definition is by configuration or programming of the learning. The number of layers or units, type of learning, and other characteristics of the model are controlled by the programmer or user. In other embodiments, one or more aspects (e.g., number of nodes, number of layers or units, or type of learning) are defined and selected by the machine during the learning. Training data, including many samples of the input scan data and the corresponding ground truths (i.e., values of the characteristics), is used to train. The relationship of the input to the output is machine learned based on the training data. Once trained, the machine-learned model (machine-learned network) may be applied to generate the prediction from input scan data for a patient.

Figure 2:
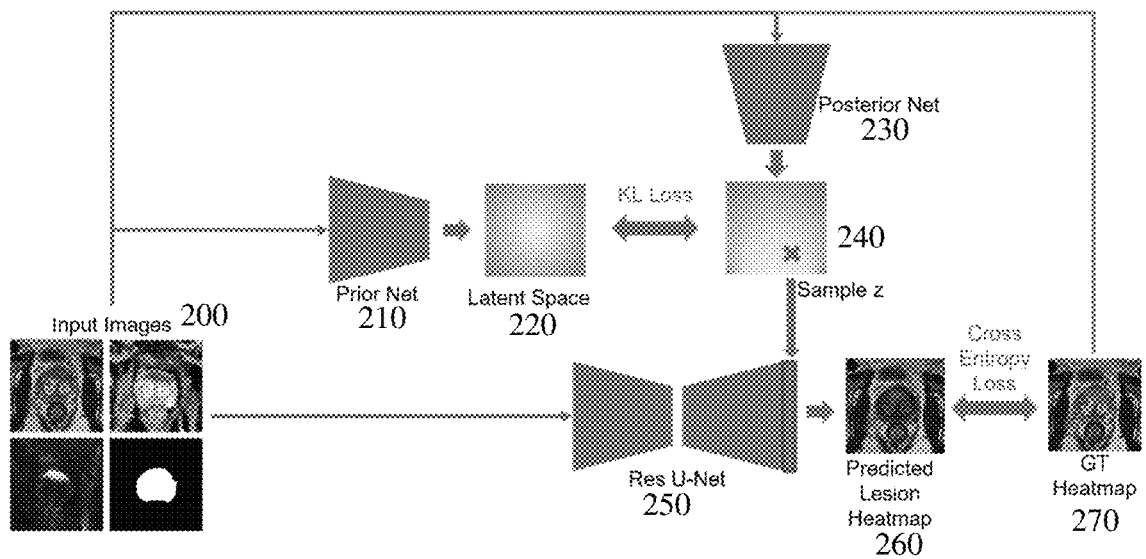
FIG. 2 shows an example architecture and machine-training arrangement for learning a distribution in latent space and segmentation prediction.

FIG. 2 shows an example model for machine training. The model is a neural network formed from a prior network 210, a posterior network 230 and a U-Net 250. This architecture uses convolutional layers and is the same or like the network used in Kohl, et al. Additional, different, or fewer components (e.g., networks) may be provided.

As taught in Kohl, et al., the U-Net 250 is a probabilistic U-Net. In another embodiment, the U-Net is a multi-scale U-Net, such as a residual U-Net (Res U-Net) or other network taught by Yu, et al. in "False Positive Reduction using Multi-scale Contextual Features for Prostate Cancer Detection in Multi-Parametric MRI Scans." In alternative embodiments, an image-to-image or another model or network is used.

The prior network 210 and/or posterior network 230 are the same or different types of networks. In one embodiment, the prior and posterior networks 210, 230 are separate encoders, such as conditional variational auto encoders. Other arrangements of convolutional or pooling layers with down-sampling may be used for the encoders. In alternative embodiments, other models (e.g., DenseNet) are used. Any regressor for generating values in a latent space from input scan data may be used.

For each encoder of the U-Net 250, prior network 210, and/or posterior network 230, a series of down sampling and convolutional layers are used, such as an encoder from a U-Net or image-to-image network. Max or other pooling layers may be included. Dropout layers may be used. The encoder increases abstraction and decreases resolution. The final layer outputs a latent representation in latent space (e.g., latent space 220 for the prior network 210, latent space 240 for the posterior network 230, and bottleneck for the U-Net 250). Values for one or more features are output by the encoder in response to input data, such as the MRI multi-parametric scan data 200. In the example of FIG. 2, the multi-parametric scan data includes T2-weighted scan data, DWI scan data, ADC scan data, and a prostate mask. The latent representations are values for features at an abstracted level relative to the input scan data 200. This latent representation is a fingerprint for the patient. The decoder of the U-Net 250 is a neural network, but other models may be used.

The neural networks are fully connected or convolutional networks. Any number of layers and nodes in layers may be used. Various layer arrangements may be used, such as sequential layers or densely connected layers. In one embodiment, some of the layers are convolutional layers. Pooling, up-sampling, down-sampling, dropout, or other layers may be used. Other architectures may be used. Different numbers of stages, layers, parameters, and/or convolutions in a layer may be used. Various kernel sizes, combinations of layers, and/or types of layers may be used.

In FIG. 2, the prior network 210, posterior network 230, and U-Net 250 are to be trained using training data of example scan data 200 and corresponding ground truths 270. The training data may be a database created for study or analysis, such as part of a clinical trial. In other approaches, the training data is created by an expert from medical records of patients. Some of the creation of the training data may be automated, such as using different segmentation algorithms to create the ground truth and/or using modeling to create synthetic samples.

FIG. 2 represents an arrangement to train the model. The image processor machine trains the model. The training learns values for weights, connections, filter kernels, and/or other learnable parameters of the defined architecture. Deep or another machine learning may be used. The weights, connections, filter kernels, and/or other parameters are the features being learned. For example, convolution kernels are features being trained. Using the training data, the values of the learnable parameters of the model are adjusted and tested to determine the values leading to an optimum estimation of the output given an input. Adam or another optimization is used to train.

The prior network 210 learns the variance of the input image or scan data 200. The posterior network 230 learns the prediction distribution of the input image or scan data 200 over ground-truth segmentation maps 270. The input scan data 200 is provided to each of the prior network 210, posterior network 230, and the U-Net 250. The posterior network 230 also receives the ground truth segmentation 270 as an input. The U-Net 250 predicts the segmentation map 260 based on the learned segmentation distribution.

A low-dimensional latent space 240 is introduced with $\mathbb{R}^N$ to encode the learned N position segmentation variances. The posterior net 230 aims to find the valuable embeddings of the distribution for predicting segmentation maps 260. The training images X (e.g., T2-weighted image, ADC, DWI, and prostate mask of scan data 200) and ground-truth segmentation map Y 270 are encoded via neural networks. The posterior net 230 learns the mapping from the segmentation variances to a Gaussian distributed latent space with the mean $\mu_{posterior}(X, Y; v) \in \mathbb{R}^N$ and variance $\sigma_{posterior}(X, Y; v) \in \mathbb{R}^N$, where v is the weight parameter (i.e., learnable parameter) of the posterior net 230. The prior net 210 learns the embeddings of the training images X (scan data 200) to estimate these segmentation variances in another latent space 220 with the probability distribution P. The distribution is modeled as axis-aligned Gaussian with mean $\mu_{prior}(X; \omega) \in \mathbb{R}^N$ and variance $\sigma_{prior}(X; \omega) \in \mathbb{R}^N$, where $\omega$ is the weight parameter (i.e., learnable parameter) of the prior net 210.

During training, the output of the posterior distribution Q (i.e., latent space 240) is randomly sampled from the distribution donated as $z \sim Q(\cdot|X, Y) = N(\mu_{posterior}(X, Y; v) \in \mathbb{R}^N, \text{diag}(\sigma_{posterior}(X, Y; v) \in \mathbb{R}^N))$. The last feature map (e.g., values of the features in the last hidden layer or another layer) from Res U-Net 250 is concatenated with the sample z from the continuous sampling of the latent space 240 and predicts the variance segmentation map S. The last layer of the feature map of the U-Net 250 is concatenated with the z sampled from the latent space 240 and predicts the semantic lesion candidate regions 260.

In training, two losses are used as the objective function for minimization. The loss between the values of features in the latent space 220 from the prior network 210 and the values of features in the latent space 240 from the posterior network 230 is one loss, and the loss between the predicted segmentation 260 and the ground truth 270 is another loss. Additional, different, or fewer losses may be used.

The loss between latent spaces 220, 240 is a Kullback-Leibler Divergence (KL loss). The KL loss is computed to pull the prior distribution and the posterior distribution to be close as possible. Thus, with input images or scan data 200 only, the prior network 210 is able to map to the distribution that is closer to the posterior distribution. The KL loss is donated as $L_{KL} = D_{KL}(Q\|P)$. Other losses between values of features in latent space may be used.

The loss between the prediction (e.g., segmentation 260) and the ground truth (e.g., ground truth segmentation 270) is a cross-entropy loss (CE loss). Considering the output of the segmentation map S as the probability of pixel-level classification, the CE loss is conducted to compare S with ground-truth Y. The CE loss is denoted as $\mathbb{E}_{z \sim Q(\cdot|X,Y)}[-\log P_c(Y|S(X,z))]$. Other losses between a prediction and ground truth may be used, such as L1 or L2 losses.

The training uses the combination of losses for joint learning. The final objective function is an average or weighted average of losses, such as a joint loss $L: L = L_{LK} + \lambda L_{CE}$ where the $\lambda$ is a relative weight factor for the losses. In alternative embodiments, the U-Net 25 is trained separately from the prior and posterior networks 210, 230, such as sequentially training in an iterative manner. Other training of other networks learning the distribution of the training data may be used.

Once trained, the machine-learned model (e.g., machine-learned network) generates a prediction (e.g., segmentation of a lesion) in response to input for a particular patient. The machine-learned model operates based on how the model was trained. Different training results in different values of learnable parameters, so results in different operation. The values of the learnable parameters are fixed or stay the same for application or testing. Given a previously unseen input, the machine-learned model generates an output (e.g., predicated segmentation 260).

Figure 3:
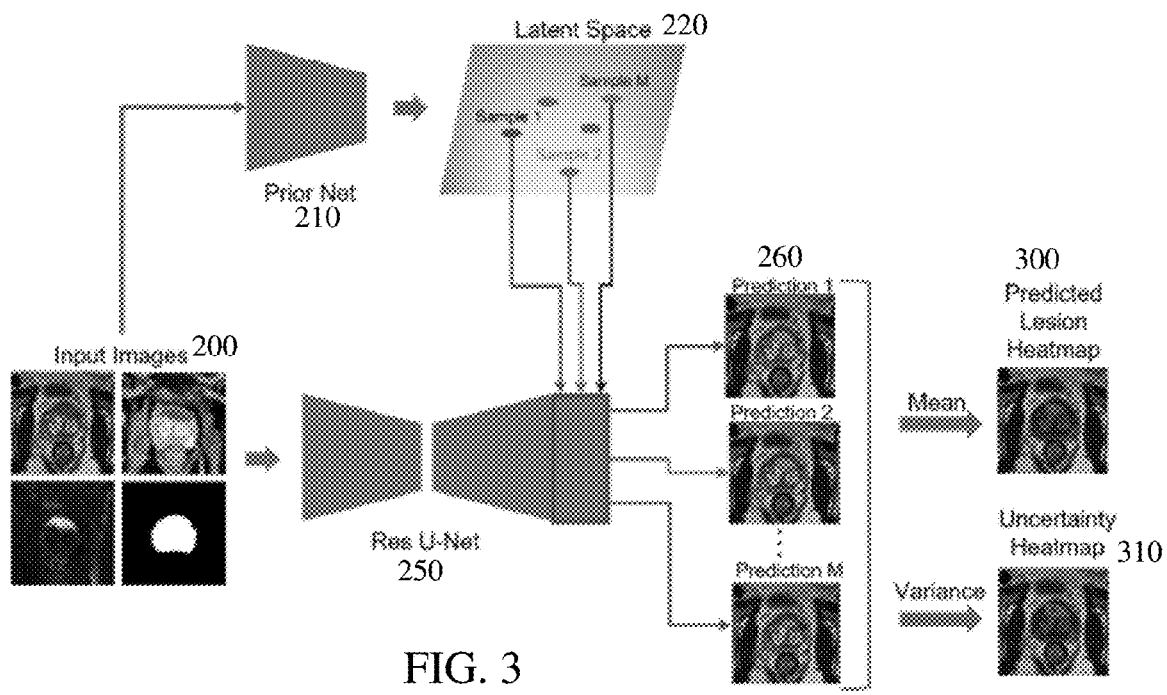
FIG. 3 shows an example architecture and testing for uncertainty determination.

FIG. 3 shows an example. The posterior network 230 is not used in testing or application. Instead, the U-Net 250 generates one or more segmentations 260 in response to input of the multi-parametric data (e.g., in response to input of the T2-weighted data, apparent diffusion coefficient data, diffusion-weighted data, and a prostate mask). The segmentation(s) 260 are generated in response to input of the multi-parametric data 200 to the U-Net 250 and the prior network 210 of the machine-learned network. The latent space 220 generated by the prior network 210 in response to input is sampled (i.e., the samples z), which samples z are concatenated with the last or other layer of the U-Net 250 to form the output segmentation or segmentations 260. The multi-parametric data 200 is input to both the U-Net 250 and the encoder of the prior network 210. The prior network 210 generates values in the latent space 220, where one or more samples of the values in the latent space 220 are provided to one of the convolutional layers of the U-Net 250. The U-Net 250 generates the segmentation 260 based in part on the input of the multi-parametric data 200 and in part on the sample z from the latent space 220. The sample z from the latent space 220 is concatenated with a last activation map of the residual U-Net 250.

Where different samples z are selected from the latent space 220, then different corresponding segmentations 260 are generated for the same scan data 200. The machine-learned model (e.g., network 210 and network 250) generates the segmentations 260 with different samples z. Any number of samples z may be selected from the latent space 220 to generate a corresponding number of segmentations 260.

In the example of FIG. 3, M predictions of segmentations 260 are generated from M different samples z from the latent space 220. The sampling from the latent space 220 may be systematic. In one embodiment, the sampling is random. The latent space 220 is randomly sampled for the M different samples z to generate the M different segmentations 260.

In another embodiment, samples z are combined. For example, a mean of selected or all samples is calculated. The mean is provided as the sample z to generate a segmentation 260. As another example, a variance of the selected or all samples is calculated. The variance is provided as the sample z to generate a segmentation 260.

In act 130 of FIG. 1, the image processor determines the uncertainty of the prediction by the machine-learned model. The quantitative uncertainty is predicted, such as in the PCa lesion detection task, to provide information to the user regarding certainty of the prediction and/or locations of the prediction with greatest or different uncertainty.

The uncertainty is determined using the machine-learned network. Rather than testing different inputs to determine uncertainty, the latent space is sampled to determine the uncertainty. Since the latent space represents a variance distribution, the latent space may be used to determine uncertainty.

In one embodiment shown in FIG. 3, the uncertainty is a variance in the segmentations 260. Multiple predictions are generated using sampling of the latent space 220. A variance of the multiple predictions is the uncertainty. Greater variance indicates greater uncertainty, and lesser variance indicates lesser uncertainty. The uncertainty may be determined spatially, such as variance for each pixel or voxel of the predicted segmentation 260. For example, the uncertainty is a spatial heat map of the variance.

The uncertainty is determined via a group of samples. As shown in FIG. 3, for the testing, a group of samples $Z_M$ are randomly selected from the latent space 220 and further concatenated with the last feature map of Res U-Net 250 to predict lesion segmentation maps $S_M$. The final prediction of the segmentation map 300 is donated as the mean, average, or other combination of the samples. For the mean, the mean segmentation S' is given as:

$$S' = \frac{1}{M}\sum_{m=1}^{M} S_M$$

and the uncertainty is defined as the variance of samples $$U = \frac{1}{M}\sum_{m=1}^{M} (S_M - S')^2.$$

Other measures of variation may be used to reflect the uncertainty. Where the prediction is not spatial, the uncertainty may be a variance calculated as a statistic.

If the testing or application images have ambiguous regions, the samples selected from latent space might have a significant variance due to the uncertainty of the encoded input images. Vice versa, if the network has high confidence to encode the segmentation variance, the predicted segmentation maps may have high correlation but vary in segmentation size or shape, especially in the boundary. The spatial representation of the uncertainty calculated from the segmentations 260 indicates these different types of uncertainty. Visual examination may be used to determine where and/or what type of uncertainty exists in the predicted segmentation or other prediction.

In one embodiment, a given number of segmentations 260 is selected and used. For example, the M different segmentations 260 are randomly selected (or M samples are randomly selected to form the M segmentations) and used to form the mean 300 and variance 310. M is any positive integer, such as 8, 16, or 32. The uncertainty is determined based on variance in the output space 260.

In another embodiment, the predicted segmentation 300 is formed by a sample z that is the mean of the values in the latent space 220 and/or by random sampling and forming a mean of the resulting segmentations 260.

In act 140 of FIG. 1, the image processor generates an image, which is displayed on a display. The display includes the prediction and/or the uncertainty. For example, an MR image is displayed. A boundary and/or region for the segmentation is overlaid or added to the image of tissue of the patient. Similarly, the uncertainty is displayed adjacent to the MR image or overlaid on a repetition of the same MR image displayed at a same time. Other display arrangements showing the prediction and uncertainty in the prediction may be used, such as one medical image of the patient with a boundary overlay showing the segmentation and a color overlay showing uncertainty by location.

In one embodiment, the prediction (e.g., mean 300 of multiple predicted segmentations 260) and the uncertainty for the prediction (e.g., variance 310) are displayed as heat maps. Color and/or intensity modulation of an MR image provide the heat map. Different colors and/or different simultaneously displayed images may be used for the segmentation and the uncertainty. In alternative embodiments, the uncertainty and/or prediction are displayed as text or a graphic, such as where the prediction is detection or classification.

Using the arrangement of FIG. 2, the networks 210, 230, 250 are trained. In the training and validation, 14 datasets are collected by a Siemens's MR scanner. Training and validation cases are conducted to train the Probabilistic U-Net 250 and the prior network 210. Seven datasets are evaluated for testing. There are 664 (47% of total testing data) in-distribution cases (i.e., cases using a same scanning or imaging configuration and same type of scanner). Additionally, 768 out-of-distribution cases (53% of total testing data) are collected from different manufactories, such as GE, with high b-values larger than 1200, from different protocols, and/or containing artifacts. Some of the out-of-distribution cases show poor performance on lesion detection results.

Figure 4:
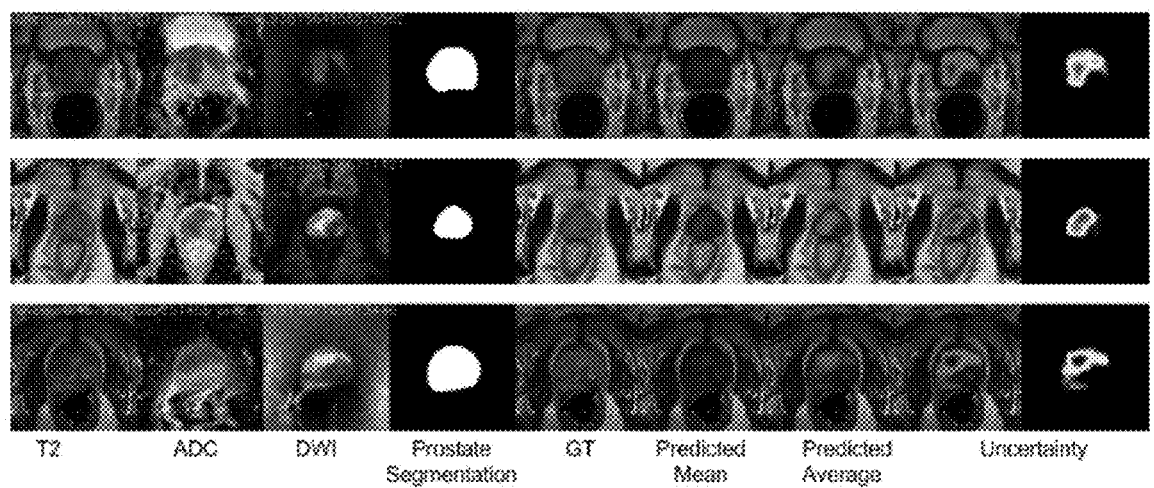
FIGS. 4 and 5 show input data examples and corresponding examples of outputs.
Figure 5:
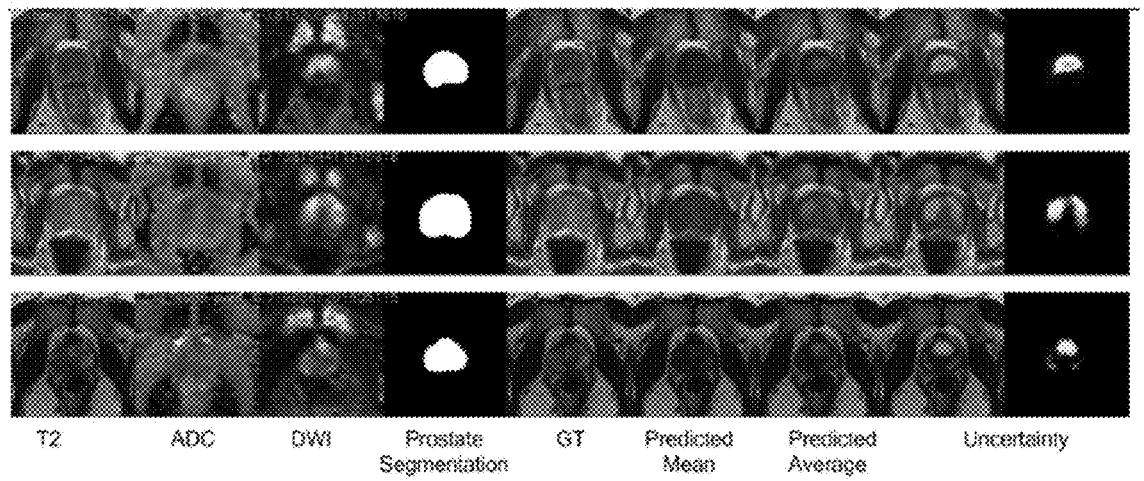

After training (i.e., for testing), the uncertainty is determined. Examples of the visualization of the uncertainty prediction is shown in FIGS. 4 and 5. The input images are T2, ADC, DWI, and prostate segmentation (first four columns). The ground truth is the ground truth of the lesion segmentation mask (fifth column). The predicted mean (sixth column) is a predicted lesion heatmap formed as a mean of the learned distribution from the latent space. The predicted average (seventh column) is the mean of 32 predicted lesion heatmaps via sampled vectors within the prostate region. The uncertainty (overly of eight column and mask of ninth column) is computed by obtaining the variance of the 32 predicted lesion heatmaps within the prostate region.

FIG. 4 illustrates three testing cases (i.e., each row is one testing case) with high uncertainty on the boundary of the predicted segmentation. The inputs, ground truth, mean, average, uncertainty as an overlay, and uncertainty as a mask are shown (rows) for each case. FIG. 5 shows the high uncertainty area over the suspicious region in the high confident segmentation prediction. Color overlay is used to show the segmentation and uncertainty. The results demonstrate the effectiveness of detecting the uncertain pixel-level lesion prediction of shape and boundaries furthermore the suspicious predicted regions. In FIG. 4, the uncertainty is greatest along the boundaries. In FIG. 5, the uncertainty is of the lesion.

Figure 6:
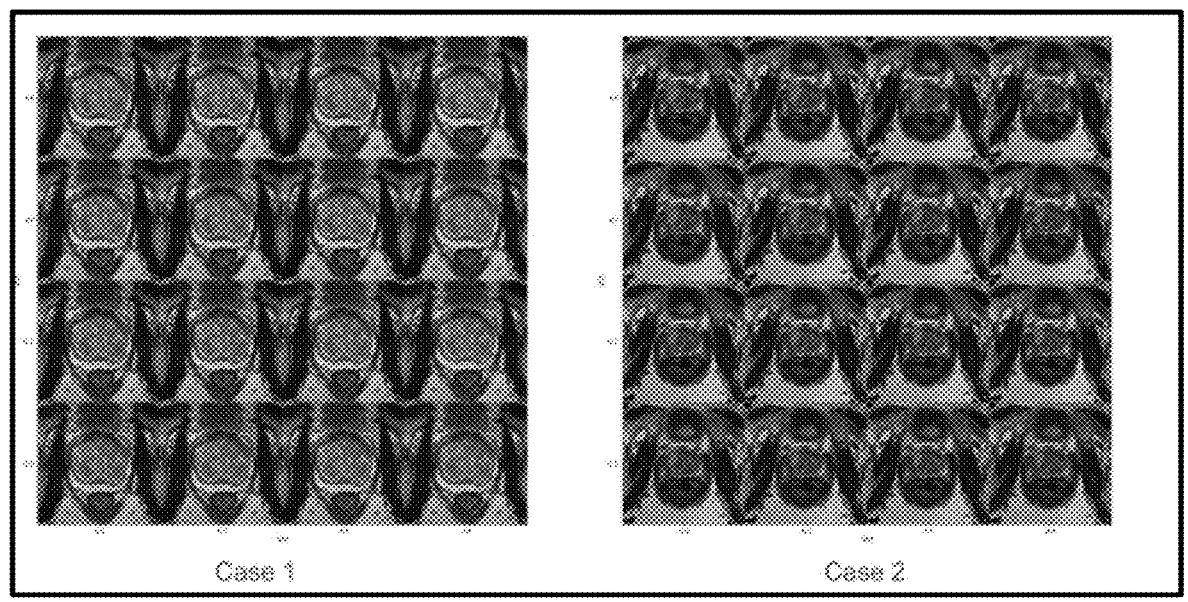
FIG. 6 shows variation in segmentation prediction for cases with high uncertainty.

FIG. 6 shows different predicted segmentations for two cases with high uncertainty (i.e., false positive). Two cases each with 16 different predicted segmentations are shown as color overlays on MR images of the prostate. The 16 different cases are for 16 randomly sampled samples z of the latent space. Two dimensions are involved in visualizing the prior sample $z_N$ in the probabilistic U-Net 250. The two cases map to a variance of 2 in $z_0$-$z_1$ latent space. The green area indicates the predicted region under different z samples. The learned variance on the space and size of the predicted region is clearly shown.

The probabilistic U-Net 250 is applied to PCa detection for uncertainty estimation. The results show the effectiveness of the model for lesion segmentation uncertainty prediction and the suspicious predicted region detection. This end-to-end training strategy can predict the lesion region, learn the segmentation variance, and detect the uncertainty region simultaneously. Further, the uncertainty map improves the PCa detection accuracy by delivery of more information to the physician.

Figure 7:
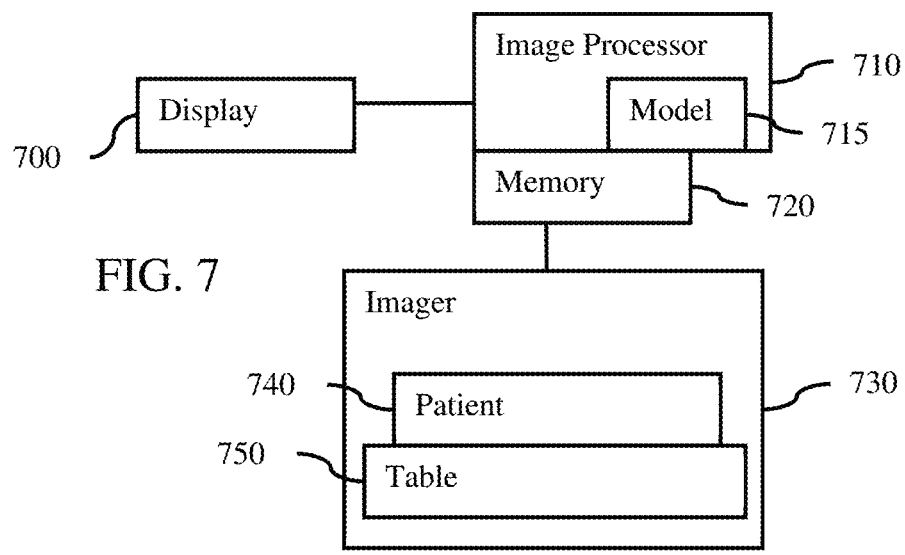
FIG. 7 is a block diagram of one embodiment of a medical system for uncertainty determination for machine-learned predictions.

FIG. 7 shows one embodiment of a medical system for uncertainty estimation. The medical system implements the method of FIG. 1 or another method.

The medical system includes the display 700, memory 720, and image processor 710. The display 700, image processor 710, and memory 720 may be part of the MR imager 730, a computer, server, workstation, or other system for image processing medical images from a scan of a patient. A workstation or computer without the MR imager 730 may be used as the medical system.

Additional, different, or fewer components may be provided. For example, a computer network is included for remote image generation of locally captured scan data or for local estimation of patient characteristics from remotely captured scan data. The machine-learned model 715 is applied as a standalone application on the workstation or a local device or as a service deployed on network (cloud) architecture. As another example, a user input device (e.g., keyboard, buttons, sliders, dials, trackball, mouse, or other device) is provided for user alteration or placement of one or more markers (e.g., landmarks) or segmentation selection or adjustment. In yet another example, the medical imager 730 is not provided.

The scan data (e.g., multi-parameter data), network definition, values of learned parameters, machine-learned model 715, feature values, values of characteristics, predictions (e.g., segmentations), uncertainty, other outputs, display image, and/or other information are stored in a non-transitory computer readable memory, such as the memory 720. The memory 720 is an external storage device, RAM, ROM, database, and/or a local memory (e.g., solid state drive or hard drive). The same or different non-transitory computer readable media may be used for the instructions and other data. The memory 720 may be implemented using a database management system (DBMS) and residing on a memory, such as a hard disk, RAM, or removable media. Alternatively, the memory 720 is internal to the processor 710 (e.g., cache).

The instructions for implementing the training or application processes, the methods, and/or the techniques discussed herein are provided on non-transitory computer-readable storage media or memories, such as a cache, buffer, RAM, removable media, hard drive, or other computer readable storage media (e.g., the memory 720). Computer readable storage media include various types of volatile and nonvolatile storage media. The functions, acts or tasks illustrated in the figures or described herein are executed by the image processor 710 in response to one or more sets of instructions stored in or on computer readable storage media. The functions, acts or tasks are independent of the particular type of instructions set, storage media, processor or processing strategy and may be performed by software, hardware, integrated circuits, firmware, micro code, and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU, or system. Because some of the constituent system components and method steps depicted in the accompanying figures may be implemented in software, the actual connections between the system components (or the process steps) may differ depending upon the way the present embodiments are programmed.

The imager 730 is a diagnostic scanner, such as an MR scanner or system. The imager 730 operates pursuant to one or more settings to scan a patient 740 resting on a bed or table 750. The settings control scanning including transmission, reception, reconstruction, and image processing. A scanning protocol is followed to generate data representing the patient 740, such as generating multi-parametric scan data representing the prostate of the patient. The patient 740 is imaged by the imager 730 using the settings. Other imagers, such as CT, PET, SPECT, or ultrasound imagers, may alternatively, or additionally, be used.

The image processor 710 is a controller, control processor, general processor, digital signal processor, three-dimensional data processor, graphics processing unit, application specific integrated circuit, field programmable gate array, artificial intelligence processor, tensor processor, digital circuit, analog circuit, combinations thereof, or another now known or later developed device for processing scan data. The image processor 710 is a single device, a plurality of devices, or a network of devices. For more than one device, parallel or sequential division of processing may be used. Different devices making up the image processor 710 may perform different functions. In one embodiment, the image processor 710 is a control processor or other processor of the medical imager 730. The image processor 710 operates pursuant to and is configured by stored instructions, hardware, and/or firmware to perform various acts described herein.

The image processor 710 or another remote processor is configured to train a machine learning architecture. Based on a user provided or other source of the network architecture and training data, the image processor 710 learns to relate one or more input variables (e.g., MR scan data) to output predictions (e.g., segmentation). The result of the training is a machine-learned network for patient modeling.

Alternatively, or additionally, the image processor 710 is configured to apply the scan data to a machine-learned network. The machine-learned network, based on past training, is configured to output a classification, detection, and/or segmentation in response to the application. For example, the machine-learned network is configured to output the segmentation as a segmentation of a lesion, such as a prostate cancer. The machine-learned network is configured to output one or a plurality of the classification, detection, and/or segmentation in response to the application of the scan data representing the patient. The outputs are generated using, in part, the random samples. The prediction (classification, detection, and/or segmentation) for display or output may be a mean, average, or other combination of multiple predictions.

The image processor is further configured to determine an uncertainty of the classification, detection, and/or segmentation with random samples from a latent space. The uncertainty is a heat map with greater uncertainty for some locations than others represented in the heat map. Other uncertainty representations may be used. The uncertainty may be a variance in output segmentations and/or a variance in the latent space. In one embodiment, the uncertainty is a variance of random samples or segmentations generated from random samples.

The machine-learned network is the U-Net and an encoder (prior network) separate from the U-Net of FIG. 3 but may be other networks. The machine-learned network is configured to generate the latent space from which latent samples are sampled for determining uncertainty.

The display 700 is a CRT, LCD, projector, plasma, printer, tablet, smart phone, or other now known or later developed display device for displaying the output, such as an image of classification, detection, and/or segmentation. In one embodiment, the display 700 displays a MR image of the prostate with a color, boundary graphic, or other designation of detection of a segment representing a lesion. The display 700 also displays the uncertainty, such as a different heatmap of color or graphic overlaying the MR image.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for lesion segmentation for a medical imager, the method comprising:
   acquiring, by the medical imager, multi-parametric data representing a patient;
   generating, by a machine-learned network, a segmentation of a lesion represented in the multi-parametric data, the segmentation generated in response to input of the multi-parametric data to the machine-learned network, wherein the machine-learned network comprises a U-Net with convolutional layers and an encoder, and wherein generating comprises inputting the multi-parametric data to both the U-Net and the encoder and feeding a sample from a latent space at an output of the encoder to one of the convolutional layers of the U-Net, the U-Net generating the segmentation based in part on the input of the multi-parametric data and in part on the sample from the latent space;
   determining an uncertainty of the segmentation, the uncertainty determined using the machine-learned network; and
   displaying the segmentation and the uncertainty of the segmentation.

2. The method of claim 1 wherein the medical imager comprises a magnetic resonance (MR) imager, and wherein acquiring comprises acquiring the multi-parametric data as T2-weighted data, apparent diffusion coefficient data, and diffusion-weighted data.

3. The method of claim 2 wherein acquiring comprises acquiring the multi-parametric data representing a prostate region of the patient, and wherein generating comprises generating the segmentation of the lesion as a prostate lesion, the segmentation of the prostate lesion generated in response to input of the T2-weighted data, apparent diffusion coefficient data, diffusion-weighted data, and a prostate mask.

4. The method of claim 1 wherein the U-Net comprises a residual U-Net and the encoder comprises a conditional variational auto encoder, and wherein generating comprises concatenating the sample from the latent space with a last activation map of the residual U-Net.

5. The method of claim 1 wherein generating comprises generating the segmentation and additional segmentations, the additional segmentations generated with different samples from the latent space.

6. The method of claim 5 wherein generating comprises generating the segmentation and additional segmentations with the different samples being randomly sampled from the latent space.

7. The method of claim 6 wherein determining the uncertainty comprises calculating a variance of the segmentation and additional segmentations, the variance being a heat map representing the uncertainty.

8. The method of claim 1 wherein the sample comprises a mean in the latent space, wherein generating the segmentation comprises generating the segmentation based in part on the mean in the latent space, and wherein determining the uncertainty comprises determining a variation in the latent space and generating a heat map by the U-Net based in part on the variation.

9. The method of claim 1 wherein generating comprises generating the segmentation and additional segmentations by the machine-learned network, and wherein determining the uncertainty comprises determining a variance of the segmentation and additional segmentations.

10. The method of claim 1 wherein displaying comprises displaying the segmentation as a mean of multiple predictions by the machine-learned network and displaying the uncertainty as a heatmap by spatial location of the segmentation.

11. A medical system for uncertainty estimation, the medical system comprising:
   an imager configured to capture scan data representing a patient;
   an image processor configured to apply the scan data to a machine-learned network, the machine-learned network configured to output a classification, detection, and/or segmentation in response to the application, the image processor further configured to determine an uncertainty of the classification, detection, and/or segmentation with random samples from a latent space, wherein the machine-learned network comprises a U-Net and an encoder separate from the U-Net, the encoder configured to generate the latent space, wherein the U-Net is configured to output a plurality of the classification, detection, and/or segmentation in response to the application of the scan data representing the patient using the random samples and wherein the uncertainty is a variance of the plurality of the classification, detection, and/or segmentation; and a display configured to display the classification, detection, and/or segmentation and to display the uncertainty.

12. The medical system of claim 11 wherein the imager comprises a magnetic resonance (MR) imager, wherein the scan data comprises multi-parametric MR data, wherein the machine-learned network is configured to output the segmentation as a segmentation of a lesion, and wherein the uncertainty is a heat map with greater uncertainty for some locations than others represented in the heat map.

13. The medical system of claim 11 wherein the display of the classification, detection, and/or segmentation is display of a mean of the plurality.

14. A medical system for uncertainty estimation, the medical system comprising:

an imager configured to capture scan data representing a patient;

an image processor configured to apply the scan data to a machine-learned network, the machine-learned network configured to output a classification, detection, and/or segmentation in response to the application, the image processor further configured to determine an uncertainty of the classification, detection, and/or segmentation with random samples from a latent space, wherein the machine-learned network comprises a U-Net and an encoder separate from the U-Net, the encoder configured to generate the latent space, wherein the uncertainty comprises the output based on a variance of the random samples; and a display configured to display the classification, detection, and/or segmentation and to display the uncertainty.

* * * * *